United States Patent
Nuñez et al.

(10) Patent No.: US 10,816,698 B2
(45) Date of Patent: Oct. 27, 2020

(54) HIGH WATER CONTENT OPHTHALMIC DEVICES

(71) Applicant: Bausch & Lomb Incorporated, Rochester, NY (US)

(72) Inventors: Ivan M. Nuñez, Penfield, NY (US); Katie L. Poetz, Webster, NY (US); Joseph W. Hoff, Fairport, NY (US); Judith Chapman Morgan, Waterford (IE)

(73) Assignee: Bausch & Lomb Incorporated, Rochester, NY (US)

( * ) Notice: Subject to any disclaimer, the term of this patent is extended or adjusted under 35 U.S.C. 154(b) by 135 days.

(21) Appl. No.: 16/100,693

(22) Filed: Aug. 10, 2018

(65) Prior Publication Data

US 2020/0049857 A1 Feb. 13, 2020

(51) Int. Cl.
| | |
|---|---|
| *G02B 1/04* | (2006.01) |
| *C07C 269/00* | (2006.01) |
| *C08F 26/10* | (2006.01) |
| *C08L 39/06* | (2006.01) |
| *G02C 7/04* | (2006.01) |
| *C08F 220/18* | (2006.01) |

(52) U.S. Cl.
CPC ............ *G02B 1/043* (2013.01); *C07C 269/00* (2013.01); *C08F 26/10* (2013.01); *C08L 39/06* (2013.01); *C08F 220/18* (2013.01); *G02C 7/04* (2013.01)

(58) Field of Classification Search
CPC .................................................... G02B 1/043
See application file for complete search history.

(56) References Cited

U.S. PATENT DOCUMENTS

| | | | |
|---|---|---|---|
| 4,436,887 | A | 3/1984 | Chromecek et al. |
| 4,528,311 | A * | 7/1985 | Beard ..................... C08F 20/36 351/159.33 |
| 4,889,664 | A | 12/1989 | Kindt-Larsen et al. |
| 5,310,779 | A | 5/1994 | Lai |
| 7,841,716 | B2 | 11/2010 | McCabe et al. |
| 7,901,073 | B2 | 3/2011 | Nunez et al. |
| 8,053,489 | B2 | 11/2011 | Nunez et al. |
| 8,138,290 | B2 | 3/2012 | Blackwell et al. |
| 8,252,850 | B2 | 8/2012 | Nunez et al. |
| 8,349,912 | B2 | 1/2013 | Nunez et al. |
| 8,377,464 | B2 | 2/2013 | Linhardt et al. |
| 2009/0191256 | A1 * | 7/2009 | Blackwell .............. G02B 1/043 424/429 |
| 2011/0105779 | A1 * | 5/2011 | Nunez ................... C08F 230/08 556/420 |
| 2017/0146823 | A1 * | 5/2017 | Lee ........................ G02C 7/049 |

FOREIGN PATENT DOCUMENTS

| | | |
|---|---|---|
| EP | 0611367 A1 | 8/1994 |
| WO | 2009094356 A1 | 7/2009 |
| WO | PCT/US18/46217 | 5/2019 |

* cited by examiner

*Primary Examiner* — Michael F Pepitone
(74) *Attorney, Agent, or Firm* — Ryan, Mason & Lewis, LLP

(57) ABSTRACT

An ophthalmic device is disclosed which is a polymerization product of a monomeric mixture comprising: (a) a major amount of one or more first non-silicone-containing hydrophilic monomers; (b) one or more hydrophobic monomers; and (c) a crosslinking agent mixture comprising (i) one or more di-, tri- or tetra(meth)acrylate-containing crosslinking agents and (ii) one or more di-, tri- or tetracarbamate-containing crosslinking agents, wherein the ophthalmic device has an equilibrium water content of at least about 65 weight percent.

23 Claims, No Drawings

HIGH WATER CONTENT OPHTHALMIC DEVICES

BACKGROUND

The present invention generally relates to ophthalmic devices such as contact lenses having a high water content.

Soft contact lenses have been available since the 1980s. It is important that contact lenses be comfortable and safe to wear. However, while there are many people who can successfully wear contact lenses, there are a number of people who can wear contact lenses for only a short period of time due to, for example, contact lens related dry eye. Symptoms of this disorder include, for example, thin and/or unstable tear films, corneal staining and subjective symptoms such as ocular discomfort, burning/stinging and dryness. Contact lens wear may trigger the onset of these symptoms or may exacerbate the symptoms.

In general, lenses with high water content have been made using allyl methacrylate (AMA) as a cross-linking agent. However, AMA is a volatile monomer and there are problems associated with its use. For example, the use of AMA can create manufacturability problems such as physical distortion as a result of post-fill-stand-down time and purging of the monomer-filled mold assembly. These problems as well as edge curling (i.e., "scalloping") during these process steps have both been shown to be related to loss of AMA.

Thus, there remains a need for a high water content ophthalmic device possessing superior dimensional stability and which avoids the problems associated with the use of AMA.

SUMMARY

In accordance with one embodiment of the present invention, an ophthalmic device is provided which is a polymerization product of a monomeric mixture comprising: (a) a major amount of one or more first non-silicone-containing hydrophilic monomers; (b) one or more hydrophobic monomers; and (c) a crosslinking agent mixture comprising (i) one or more di-, tri- or tetra(meth)acrylate-containing crosslinking agents and (ii) one or more di-, tri- or tetracarbamate-containing crosslinking agents, wherein the ophthalmic device has an equilibrium water content of at least about 65 weight percent.

In accordance with a second embodiment of the present invention, a method is provided for making an ophthalmic device which comprises (a) providing a monomeric mixture comprising (i) a major amount of one or more first non-silicone-containing hydrophilic monomers; (ii) one or more hydrophobic monomers; and (iii) a crosslinking agent mixture comprising (1) one or more di-, tri- or tetra(meth)acrylate-containing crosslinking agents and (2) one or more di-, tri- or tetracarbamate-containing crosslinking agents; (b) subjecting the monomeric mixture to polymerizing conditions to provide a polymerized device, and (c) hydrating the polymerized device, wherein the device has an equilibrium water content of at least about 65 weight percent.

The high water content ophthalmic devices of the present invention advantageously possess an improved modulus without using AMA in forming the devices by polymerizing a monomeric mixture comprising: (a) a major amount of one or more first non-silicone-containing hydrophilic monomers; (b) one or more hydrophobic monomers; and (c) a crosslinking agent mixture comprising (i) one or more di-, tri- or tetra(meth)acrylate-containing crosslinking agents and (ii) one or more di-, tri- or tetracarbamate-containing crosslinking agents, wherein the ophthalmic device has an equilibrium water content of at least about 65 weight percent. In addition, by employing a crosslinking agent mixture comprising (i) one or more di- or tri(meth)acrylate-containing crosslinking agents and (ii) one or more di- or tri-carbamate-containing crosslinking agents in the monomeric mixture to form the high water content ophthalmic devices herein, improved dimensional stability, lower extractables, and improved tear resistance can be achieved in the absence of AMA as a crosslinking agent.

DETAILED DESCRIPTION

The illustrative embodiments described herein are directed to high water content ophthalmic devices. Although the illustrative embodiments are applicable to a variety of high water content ophthalmic devices, one particular illustrative embodiment is especially useful and advantageous for high water content contact lenses. As used herein, the terms "opthalmic device" and "lens" refer to devices that reside in or on the eye. These devices can provide optical correction, wound care, drug delivery, diagnostic functionality or cosmetic enhancement or any combination of these properties. Representative examples of such devices include, but are not limited to, soft contact lenses, e.g., soft, hydrogel lenses, soft, non-hydrogel lenses and the like, intraocular lenses, overlay lenses, ocular inserts, optical inserts, bandage lenses and therapeutic lenses and the like. As is understood by one skilled in the art, a lens is considered to be "soft" if it can be folded back upon itself without breaking. The high water content ophthalmic devices such as high water content contact lenses of the illustrative embodiments can be spherical, toric, bifocal, may contain cosmetic tints, opaque cosmetic patterns, combinations thereof and the like.

In one illustrative embodiment, a high water content ophthalmic device will have an equilibrium water content of at least about 65 weight percent. In another illustrative embodiment, the high water content ophthalmic devices will have an equilibrium water content of at least about 70 weight percent. In another illustrative embodiment, the high water content ophthalmic devices will have an equilibrium water content of at least about 75 weight percent. In general, the high water content ophthalmic devices are a polymerization product of a monomeric mixture comprising: (a) a major amount of one or more first non-silicone-containing hydrophilic monomers; (b) one or more hydrophobic monomers; and (c) a crosslinking agent mixture comprising (i) one or more di-, tri- or tetra(meth)acrylate-containing crosslinking agents and (ii) one or more di-, tri- or tetracarbamate-containing crosslinking agents, wherein the ophthalmic device has an equilibrium water content of at least about 65 weight percent. In one illustrative embodiment, the monomeric mixture contains no silicone-containing monomer.

In general, suitable non-silicone-containing hydrophilic monomers include amides, cyclic lactams, poly(alkene glycols) functionalized with polymerizable groups and the like and mixtures thereof. Representative examples of amides include alkylamides such as N,N-dimethylacrylamide, N,N-dimethylmethacrylamide and the like and mixtures thereof. Representative examples of cyclic lactams such as N-vinyl-2-pyrrolidone, N-vinyl caprolactam, N-vinyl-2-piperidone and the like and mixtures thereof. Representative examples of functionalized poly(alkene glycols) include poly(diethylene glycols) of varying chain length containing monomethacrylate or dimethacrylate end caps. In one embodiment, the poly(alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. Mixtures of the foregoing non-silicone-containing hydrophilic monomers can also be used in the monomeric mixtures herein.

In one preferred embodiment, the one or more first non-silicone-containing hydrophilic monomers are one or more cyclic lactams such as N-vinyl-2-pyrrolidone. In another embodiment, the one or more cyclic lactams are present in the monomeric mixture in a major amount, e.g., an amount of at least about 70 weight percent or an amount of at least about 70 weight percent and up to about 95 weight percent or an amount of at least about 80 weight percent, or an amount of at least about 80 weight percent and up to about 95 weight percent based on the total weight of the monomeric mixture.

In another embodiment, the monomeric mixture further includes one or more second non-silicone-containing hydrophilic monomers in a minor amount. In one embodiment, the monomeric mixture further includes one or more amides in a minor amount. In another embodiment, the monomeric mixture further includes N,N-dimethylacrylamide in a minor amount.

In general, a minor amount of the one or more second non-silicone-containing hydrophilic monomers is an amount of less than or equal to about 10 weight percent, e.g., an amount ranging from about 0.25 to about 10 weight percent, based on the total weight of the monomeric mixture.

In another embodiment, the monomeric mixture includes a major amount one or more first non-silicone-containing hydrophilic monomers which are one or more cyclic lactams such as N-vinyl-2-pyrrolidone, and a minor amount of one or more second non-silicone-containing hydrophilic monomers. In one embodiment, the monomeric mixture includes a major amount of one or more first non-silicone-containing hydrophilic monomers which are one or more cyclic lactams such as N-vinyl-2-pyrrolidone, and a minor amount of one or more second non-silicone-containing hydrophilic monomers which are one or more amides such as N,N-dimethylacrylamide. In one embodiment, the monomeric mixture includes (a) at least about 70 weight percent, based on the total weight of the monomeric mixture, of one or more first non-silicone-containing hydrophilic monomers which are one or more cyclic lactams such as N-vinyl-2-pyrrolidone, and (b) less than or equal to about 10 weight percent, based on the total weight of the monomeric mixture, of one or more second non-silicone-containing hydrophilic monomers which are one or more amides such as N,N-dimethylacrylamide.

The monomeric mixture further includes one or more hydrophobic monomers. Suitable hydrophobic monomers (b) include ethylenically unsaturated hydrophobic monomers such as, for example, (meth)acrylates-containing hydrophobic monomers, N-alkyl (meth)acrylamides-containing hydrophobic monomers, alkyl vinylcarbonates-containing hydrophobic monomers, alkyl vinylcarbamates-containing hydrophobic monomers, fluoroalkyl (meth) acrylates-containing hydrophobic monomers, N-fluoroalkyl (meth)acrylamides-containing hydrophobic monomers, N-fluoroalkyl vinylcarbonates-containing hydrophobic monomers, N-fluoroalkyl vinylcarbamates-containing hydrophobic monomers, silicone-containing (meth)acrylates-containing hydrophobic monomers, (meth)acrylamides-containing hydrophobic monomers, vinyl carbonates-containing hydrophobic monomers, vinyl carbamates-containing hydrophobic monomers, styrenic-containing hydrophobic monomers, polyoxypropylene (meth)acrylate-containing hydrophobic monomers and the like and mixtures thereof. As used herein, the term "(meth)" denotes an optional methyl substituent. Thus, terms such as "(meth) acrylate" denotes either methacrylate or acrylate, and "(meth)acrylamide" denotes either methacrylamide or acrylamide.

In one illustrative embodiment, wherein the one or more hydrophobic monomers is represented by the structure of Formula I:

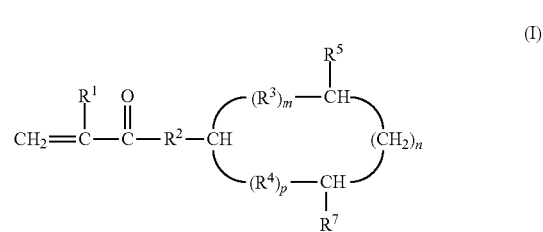

(I)

wherein $R^1$ is methyl or hydrogen; $R^2$ is —O— or —NH—; $R^3$ and $R^4$ are independently a divalent radical selected from the group consisting of —$CH_2$—, —CHOH— and —$CHR^6$—; $R^5$ and $R^6$ are independently a branched $C_3$-$C_8$ alkyl group; $R^7$ is hydrogen or —OH; n is an integer of at least 1, and m and p are independently 0 or an integer of at least 1, provided that the sum of m, p and n is 2, 3, 4 or 5.

Representative examples of one or more hydrophobic monomers (b) represented by the structure of Formula I include, but are not limited to, 4-t-butyl-2-hydroxycyclohexyl methacrylate (TBE); 4-t-butyl-2-hydroxycyclopentyl methacrylate; butyl-2-hydroxycyclohexyl methacrylamide (TBA); 6-isopentyl-3-hydroxycyclohexyl methacrylate; 2-isohexyl-5-hydroxycyclopentyl methacryl amide, 4-t-butylcyclohexyl methacrylate, isobornyl methacrylate, adamantyl methacrylate, n-butyl methacrylate, n-hexyl methacrylate, lauryl methacrylate, benzyl methacrylate, and the like. In one embodiment, one or more hydrophobic monomers (b) include compounds of formula I wherein $R^3$ is —$CH_2$—, m is 1 or 2, p is 0, and the sum of m and n is 3 or 4.

The one or more hydrophobic monomers (b) will ordinarily be present in the monomeric mixture in an amount ranging from about 0.5 to about 25 or from about 1 to about 10 weight percent, based on the total weight of the monomeric mixture.

The monomeric mixture further includes a crosslinking agent mixture comprising (i) one or more di-, tri- or tetra (meth)acrylate-containing crosslinking agents and (ii) one or more di-, tri- or tetracarbamate-containing crosslinking agents. In one illustrative embodiment, useful one or more di-, tri- or tetra(meth)acrylate-containing crosslinking agents include alkanepolyol di-, tri- or tetra(meth)acrylate-containing crosslinking agents such as, for example, one or more alkylene glycol di(meth)acrylate crosslinking agents, one or more alkylene glycol tri(meth)acrylate crosslinking agents, one or more alkylene glycol tetra(meth)acrylate crosslinking agents, one or more alkanediol di(meth)acrylate crosslinking agents, alkanediol tri(meth)acrylate crosslinking agents, alkanediol tetra(meth)acrylate crosslinking agents, agents, one or more alkanetriol di(meth)acrylate crosslinking agents, alkanetriol tri(meth)acrylate crosslinking agents, alkanetriol tetra(meth)acrylate crosslinking agents, agents, one or more alkanetetraol di(meth)acrylate crosslinking agents, alkanetetraol tri(meth)acrylate crosslinking agents, alkanetetraol tetra(meth)acrylate crosslinking agents and the like and mixtures thereof. In one embodiment, one or more alkylene glycol di(meth)acrylate crosslinking agents include ethylene glycol di(meth)acrylates having up to about 10 ethylene glycol repeating units, butyleneglycol di(meth)acrylate and the like. In one embodiment, one or more alkanediol di(meth)acrylate crosslinking agents include butanediol di(meth)acrylate crosslinking agents, hexanediol di(meth)acrylate and the like. In one embodiment, one or more alkanetriol tri(meth)acrylate crosslinking agents are trimethylol propane trimethacrylate crosslinking agents. In one embodiment, one or more alkanetetraol tetra(meth)acrylate crosslinking agents are pentaerythritol tetramethacrylate crosslinking agents.

In one illustrative embodiment, useful one or more di-, tri- or tetracarbamate-containing crosslinking agents include one or more di(N-vinylcarbamate)-containing crosslinking agents, one or more di(N-allylcarbamate)-containing crosslinking agents, one or more di(O-vinylcarbamate)-containing crosslinking agents, one or more di(O-allylcarbamate)-containing crosslinking agents, one or more tri(N-vinylcarbamate)-containing crosslinking agents, one or more tri(N-allylcarbamate)-containing crosslinking agents, one or more tri(O-vinylcarbamate)-containing crosslinking agents, one or more tri(O-allylcarbamate)-containing crosslinking agents, one or more tetra(N-vinylcarbamate)-containing crosslinking agents, one or more tetra (N-allylcarbamate)-containing crosslinking agents, one or more tetra (O-vinylcarbamate)-containing crosslinking agents, one or more tetra(O-allyl carbamate)-containing crosslinking agents, and the like and mixtures thereof.

In one embodiment, one or more di-carbamate-containing crosslinking agents include bis (N-vinyl carbamates) having the following structure:

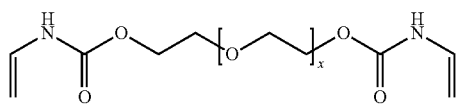

wherein x is from 0 to 10.

In one embodiment, one or more di-carbamate-containing crosslinking agents include bis (O-vinyl carbamates) having the following structure:

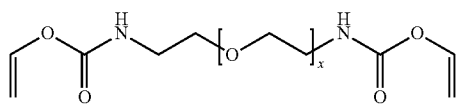

wherein x is from 0 to 10.

In one embodiment, one or more di-carbamate-containing crosslinking agents include diethylene glycol bis(N-vinylcarbamate), diethylene glycol bis(O-allylcarbamate), and the like and mixtures thereof.

In general, the one or more di-, tri- or tetra(meth)acrylate-containing crosslinking agents are present in the monomeric mixture in an amount of about 0.1 to about 10.0 weight percent, based on the total weight of the monomer mixture, and the one or more di-, tri- or tetracarbamate-containing crosslinking agents are present in the monomer mixture in an amount of about 0.1 to about 5.0 weight percent, based on the total weight of the monomer mixture.

In another illustrative embodiment, the monomeric mixture further includes one or more end terminal functionalized surfactants. A suitable end terminal functionalized surfactant includes, by way of example, one or more end terminal functionalized polyethers. Useful polyethers to be end terminal functionalized comprise one or more chains or polymeric components which have one or more (—O—R—) repeats units wherein R is an alkylene or arylene group having 2 to about 6 carbon atoms. The polyethers may be derived from block copolymers formed from different ratio components of ethylene oxide (EO) and propylene oxide (PO). Such polyethers and their respective component segments may include different attached hydrophobic and hydrophilic chemical functional group moieties and segments.

A representative example of a suitable polyether which can be end terminal functionalized is a poloxamer block copolymer. One specific class of poloxamer block copolymers are those available under the trademark Pluronic (BASF Wyandotte Corp., Wyandotte, Mich.). Poloxamers include Pluronics and reverse Pluronics. Pluronics are a series of ABA block copolymers composed of poly(ethylene oxide)-poly(propylene oxide)-poly(ethylene oxide) blocks as generally represented in Formula VII:

$$HO(C_2H_4O)_a(C_3H_6O)_b(C_2H_4O)_aH \qquad (VII)$$

wherein a is independently at least 1 and b is at least 1.

Reverse Pluronics are a series of BAB block copolymers, respectively composed of poly(propylene oxide)-poly(ethylene oxide)-poly(propylene oxide) blocks as generally represented in Formula VIII:

$$HO(C_3H_6O)_b(C_2H_4O)_a(C_3H_6O)_bH \qquad (VIII)$$

wherein a is at least 1 and b is independently at least 1. The poly(ethylene oxide), PEO, blocks are hydrophilic, whereas the poly(propylene oxide), PPO, blocks are hydrophobic in nature. The poloxamers in each series have varying ratios of PEO and PPO which ultimately determines the hydrophilic-lipophilic balance (HLB) of the material, i.e., the varying HLB values are based upon the varying values of a and b, a representing the number of hydrophilic poly(ethylene oxide) units (PEO) being present in the molecule and b representing the number of hydrophobic poly(propylene oxide) units (PPO) being present in the molecule.

Poloxamers and reverse poloxamers have terminal hydroxyl groups that can be terminal functionalized. An example of a terminal functionalized poloxamer and as discussed hereinbelow is poloxamer dimethacrylate (e.g., Pluronic® F127 dimethacrylate) as disclosed in U.S. Patent Application Publication No. 2003/0044468. Other examples include glycidyl-terminated copolymers of polyethylene glycol and polypropylene glycol as disclosed in U.S. Pat. No. 6,517,933.

Another example of a suitable polyether which can be end terminal functionalized is a poloxamine block copolymer. While the poloxamers and reverse poloxamers are considered to be difunctional molecules (based on the terminal hydroxyl groups), the poloxamines are in a tetrafunctional form, i.e., the molecules are tetrafunctional block copolymers terminating in primary hydroxyl groups and linked by a central diamine. One specific class of poloxamine block copolymers are those available under the trademark Tetronic (BASF). Poloxamines include Tetronic and reverse Tetronics. Poloxamines have the following general structure of Formula IX:

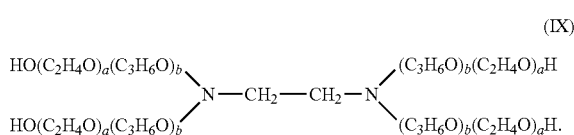

(IX)

wherein a is independently at least 1 and b is independently at least 1.

The poloxamer and/or poloxamine is functionalized to provide the desired reactivity at the end terminal of the molecule. The functionality can be varied and is determined based upon the intended use of the functionalized PEO- and PPO-containing block copolymers. That is, the PEO- and PPO-containing block copolymers are reacted to provide end terminal functionality that is complementary with the intended device forming monomeric mixture. The term block copolymer as used herein shall be understood to mean a poloxamer and/or poloxamine as having two or more blocks in their polymeric backbone(s).

Generally, selection of the functional end group is determined by the functional group of the reactive molecule(s) in the monomeric mixture. For example, if the reactive molecule contains a carboxylic acid group, glycidyl methacrylate can provide a methacrylate end group. If the reactive molecule contains hydroxy or amino functionality, isocyanato ethyl methacrylate or (meth)acryloyl chloride can provide a methacrylate end group and vinyl chloro formate can provide a vinyl end group. A wide variety of suitable combinations of ethylenically unsaturated end groups and reactive molecules will be apparent to those of ordinary skill in the art. For example, the functional group may comprise a moiety selected from amine, hydrazine, hydrazide, thiol (nucleophilic groups), carboxylic acid, carboxylic ester, including imide ester, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, halosilane, and phosphoramidate. More specific examples of these groups include succinimidyl ester or carbonate, imidazolyl ester or carbonate, benzotriazole ester or carbonate, p-nitrophenyl carbonate, vinyl sulfone, chloroethylsulfone, vinylpyridine, pyridyl disulfide, iodoacetamide, glyoxal, dione, mesylate, tosylate, and tresylate. Also included are other activated carboxylic acid derivatives, as well as hydrates or protected derivatives of any of the above moieties (e.g. aldehyde hydrate, hemiacetal, acetal, ketone hydrate, hemiketal, ketal, thioketal, thioacetal). Preferred electrophilic groups include succinimidyl carbonate, succinimidyl ester, maleimide, benzotriazole carbonate, glycidyl ether, imidazoyl ester, p-nitrophenyl carbonate, acrylate, tresylate, aldehyde, and orthopyridyl disulfide.

Representative examples of reaction sequences by which PEO- and PPO-containing block copolymers can be end-functionalized are provided below.

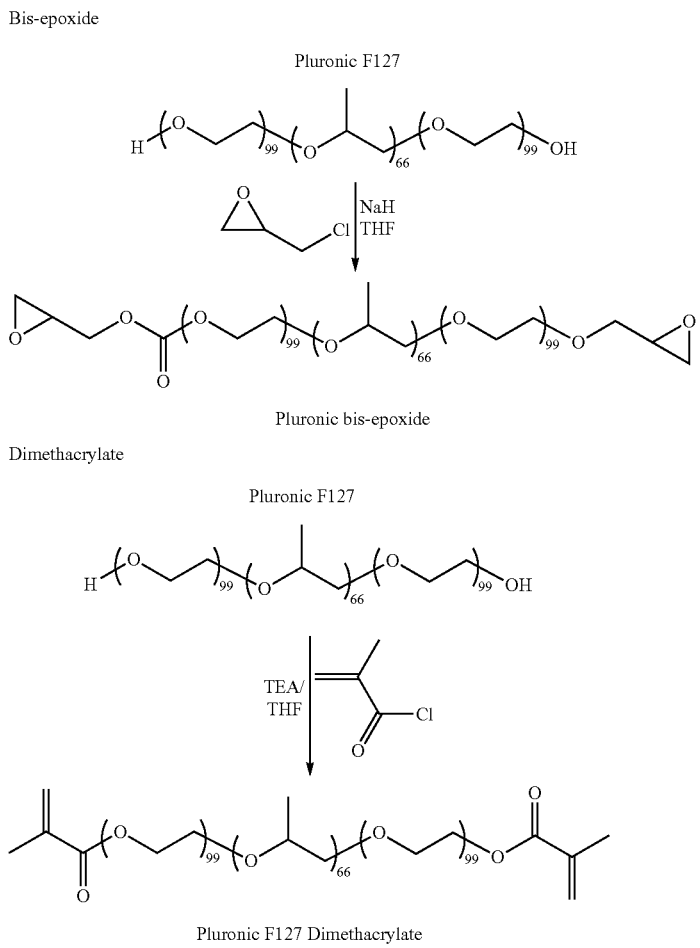

Diisocyanate

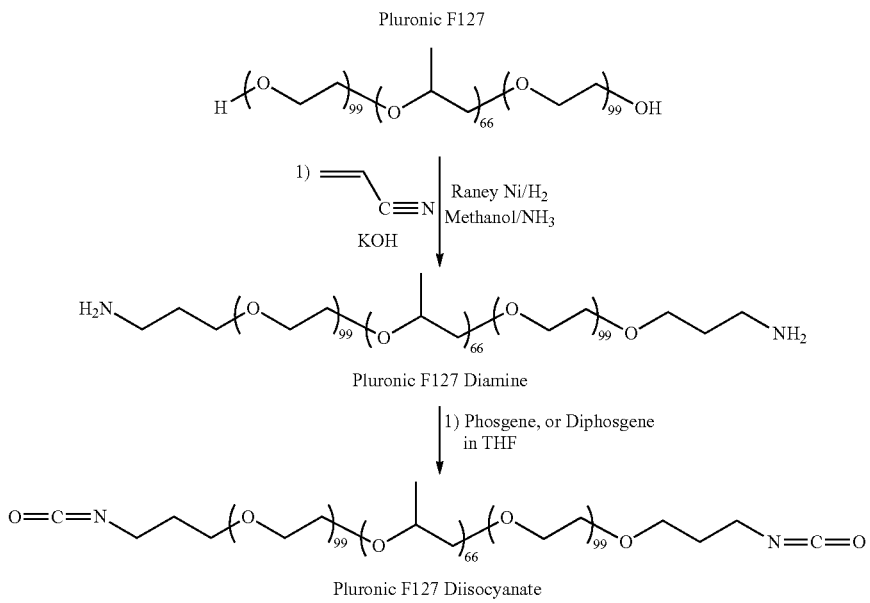

Pluronic F127 Diisocyanate

Further provided herein are certain exemplary, but non-limiting, examples of reactions for providing functionalized termini for PEO- and PPO-containing block copolymers. It is to be understood that one of ordinary skill in the art would be able to determine other reaction methods without engaging in an undue amount of experimentation. It should also be understood that any particular block copolymer molecule shown is only one chain length of a polydispersed population of the referenced material.

In one preferred embodiment, the monomeric mixture include one or more of PEO- and PPO-containing block copolymers. An example of such a copolymer that can be used in monomeric mixture is Pluronic® F127, a block copolymer having the structure [(polyethylene oxide)$_{99}$-(polypropylene oxide)$_{66}$-(polyethylene oxide)$_{99}$]. The terminal hydroxyl groups of the copolymer are functionalized to allow for the reaction of the copolymer with other ophthalmic device forming monomers. Another example includes Pluronic 407 dimethacrylate having the following structure

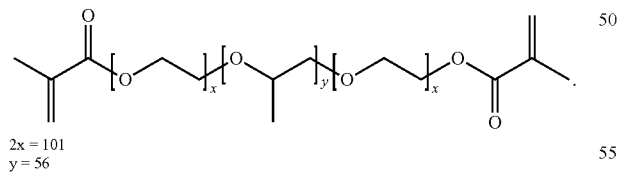

$2x = 101$
$y = 56$

In one embodiment, an end terminal functionalized surfactant is selected from the group consisting of poloxamers having at least one end terminal functionalized, reverse poloxamers having at least one end terminal functionalized, poloxamines having at least one end terminal functionalized, reverse poloxamines having at least one end terminal functionalized and mixtures thereof.

Generally, the end terminal functionalized surfactants will be present in the monomeric mixtures in an amount ranging from about 0.01 to about 20 weight percent, or from about 1 to about 10 weight percent, or from about 3 to about 6 weight percent, based on the total weight of the monomeric mixture.

In another illustrative embodiment, the monomeric mixture further includes one or more ultraviolet (UV) blockers. In one embodiment, useful UV blockers include one or more compounds of the following formula:

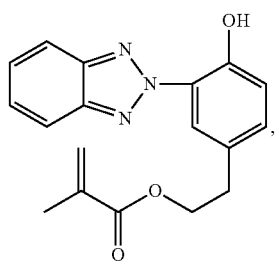

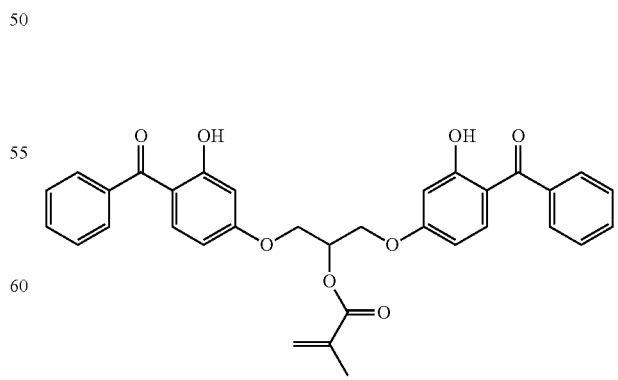

(2-Propenoic acid, 2-methyl, 2-(4-benzoyl-3-hydroxyphenoxy)-1-[(4-benzoyl3-hydroxyphenoxy)methyl ester),

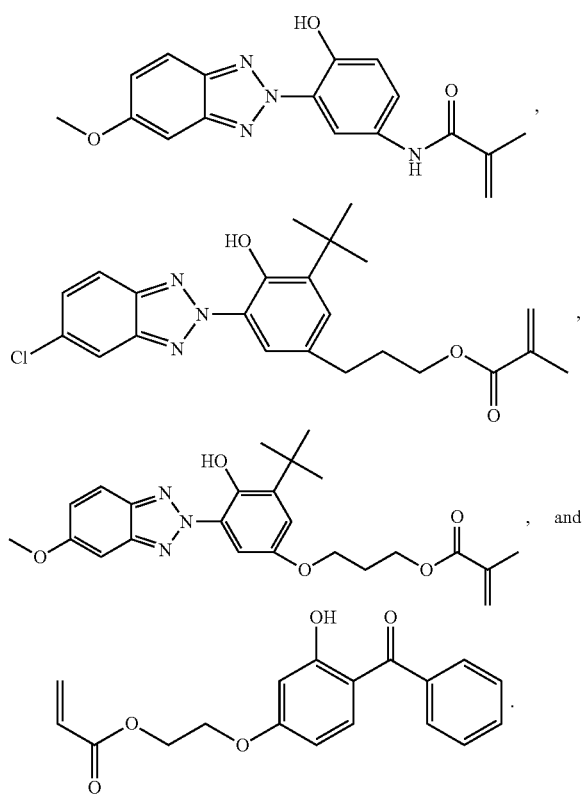

The monomeric mixture may further contain, as necessary and within limits not to impair the purpose and effect of the present invention, various additives such as an antioxidant, coloring agent, lubricant internal wetting agents, toughening agents and the like and other constituents as is well known in the art.

The ophthalmic devices of the illustrative embodiments, e.g., contact lenses or intraocular lenses, can be prepared by polymerizing the foregoing monomeric mixtures to form a product that can be subsequently formed into the appropriate shape by, for example, lathing, injection molding, compression molding, cutting and the like. For example, in producing contact lenses, the initial mixture may be polymerized in tubes to provide rod-shaped articles, which are then cut into buttons. The buttons may then be lathed into contact lenses.

Alternately, the ophthalmic devices such as contact lenses may be cast directly in molds, e.g., polypropylene molds, from the mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the mixtures to be polymerized to a mold, and spinning the mold in a controlled manner while exposing the mixture to a radiation source such as UV light. Static casting methods involve charging the monomeric mixture between two mold sections, one mold section shaped to form the anterior lens surface and the other mold section shaped to form the posterior lens surface, and curing the mixture while retained in the mold assembly to form a lens, for example, by free radical polymerization of the mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a monomeric mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetyl peroxide, lauroyl peroxide, decanoyl peroxide, stearoyl peroxide, benzoyl peroxide, tertiarylbutyl peroxypivalate, peroxydicarbonate, and the like. Representative UV initiators are those known in the art and include benzoin methyl ether, benzoin ethyl ether, Darocure® 1173, 1164, 2273, 1116, 2959, 3331 (EM Industries) and Irgacure® 651 and 184 (Ciba-Geigy), 2,2'Azobis(2-methylpropionitrile) (VAZO 64) and the like. Generally, the initiator will be employed in the monomeric mixture at a concentration of about 0.01 to about 5 percent by weight of the total mixture.

Polymerization is generally performed in a reaction medium, such as, for example, a solution or dispersion using a solvent, e.g., water or an alkanol containing from 1 to 4 carbon atoms such as methanol, ethanol or propan-2-ol. Alternatively, a mixture of any of the above solvents may be used.

Generally, polymerization can be carried out for about 15 minutes to about 72 hours, and under an inert atmosphere of, for example, nitrogen or argon. If desired, the resulting polymerization product can be dried under vacuum, e.g., for about 5 to about 72 hours or left in an aqueous solution prior to use.

Polymerization of the mixtures will yield a polymer, that when hydrated, preferably forms a hydrogel. When producing a hydrogel lens, the mixture may further include at least a diluent that is ultimately replaced with water when the polymerization product is hydrated to form a hydrogel. Generally, the water content of the hydrogel is as described hereinabove, i.e., at least about 65 weight percent. The amount of diluent used should be less than about 50 weight percent and in most cases, the diluent content will be less than about 30 weight percent. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; and the like and mixtures thereof.

If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired, the mixture used to produce the hydrogel lens may further include crosslinking and wetting agents known in the prior art for making hydrogel materials.

In the case of intraocular lenses, the monomeric mixtures to be polymerized may further include a monomer for increasing the refractive index of the resultant polymerized product. Examples of such monomers include aromatic (meth) acrylates, such as phenyl (meth)acrylate, 2-phenylethyl (meth)acrylate, 2-phenoxyethyl methacrylate, and benzyl (meth)acrylate.

The ophthalmic devices such as contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative. The examples should not be read as limiting the scope of the invention as defined in the claims.

Various polymerization products were formed as discussed below and characterized by standard testing procedures such as:

Water %: Two sets of six hydrated lenses or films are blotted dry on a piece of filter paper to remove excess water, and samples are weighed (wet weight). Samples are then placed in a microwave oven for 10 minutes inside ajar containing desiccant. The samples are then allowed to sit for 30 minutes to equilibrate to room temperature and reweighed (dry weight). The percent water is calculated from the wet and dry weights.

Contact Angle: Captive bubble contact angle data was collected on a First Ten Angstroms FTA-1000 prop Shape Instrument. All samples were rinsed in HPLC grade water prior to analysis in order to remove components of the packaging solution from the sample surface. Prior to data collection the surface tension of the water used for all experiments was measured using the pendant drop method. In order for the water to qualify as appropriate for use, a surface tension value of 70-72 dynes/cm was expected. All lens samples were placed onto a curved sample holder and submerged into a quartz cell filled with HPLC grade water. Advancing and receding captive bubble contact angles were collected for each sample. The advancing contact angle is defined as the angle measured in water as the air bubble is retracting from the lens surface (water is advancing across the surface). All captive bubble data was collected using a high speed digital camera focused onto the sample/air bubble interface. The contact angle was calculated at the digital frame just prior to contact line movement across the sample/air bubble interface. The receding contact angle is defined as the angle measured in water as the air bubble is expanding across the sample surface (water is receding from the surface).

Modulus (g/mm$^2$) and % elongation were measured per ASTM 1708 employing an Instron (Model 4502) instrument where the film sample was immersed in borate buffered saline; an appropriate size of the film sample was gauge length 22 mm and width 4.75 mm, where the sample further has ends forming a dogbone shape to accommodate gripping of the sample with clamps of the Instron instrument, and a thickness of 100±50 microns.

Tensile strength (g/mm$^2$) was measured per ASTM test method D1708a.

Tear strength was measured according to ASTM D-1938 under the same physical conditions as for tensile modulus.

Sagittal depth (SAG) as measured on a Deltronic Comparator.

Refractive index (RI) was measured per typical methods on hydrated samples using a refractometer.

In the examples, the following abbreviations are used.
DMA: N,N-dimethylacrylamide
HEMA: 2-hydroxyethyl methacrylate
NVP: N-vinyl-2-pyrrolidone
AMA: Allyl methacrylate
EGDMA: Ethylene glycol dimethacrylate
Vazo™ 64: azo bis-isobutylnitrile (AIBN)
CIX-4: a compound having the structure:

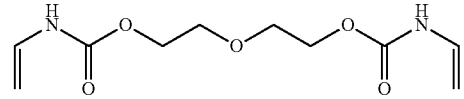 [SMILES: C=CNC(=O)OCCOCCOC(=O)NC=C]

SA monomer: a compound having the structure:

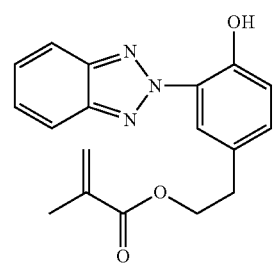 [SMILES: C=C(C)C(=O)OCCc1ccc(O)c(-n2nc3ccccc3n2)c1]

Poloxamer: Pluronic 407 dimethacrylate having the following structure

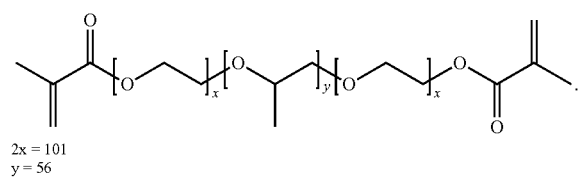

2x = 101
y = 56

Comparative Examples A-F

A monomer mix was made by mixing the following components, listed in Table 1 at amounts per weight.

TABLE 1

| Formulation | Comp. Ex. A | Comp. Ex. B | Comp. Ex. C | Comp. Ex. D | Comp. Ex. E | Comp. Ex. F |
|---|---|---|---|---|---|---|
| NVP | 90 | 90 | 90 | 90 | 90 | 90 |
| TBE | 10 | 10 | 10 | 10 | 10 | 10 |
| HEMA | 2 | 2 | 2 | 2 | 2 | 2 |
| EGDMA | 0.13 | 0.13 | 0.13 | 0.13 | 0.13 | 0.13 |
| AMA | 0 | 0.25 | 0.5 | 0.75 | 0.88 | 1 |
| Poloxamer 407 Dimethacrylate | 5 | 5 | 5 | 5 | 5 | 5 |
| SA Monomer | 2 | 2 | 2 | 2 | 2 | 2 |
| Propylene Glycol | 10 | 10 | 10 | 10 | 10 | 10 |
| Vazo 64 | 0.5 | 0.5 | 0.5 | 0.5 | 0.5 | 0.5 |
| TINT | 0.02 | 0.02 | 0.02 | 0.02 | 0.02 | 0.02 |
| Properties | | | | | | |
| Water Content (%) | 80.9 | 79.8 | 77.7 | 76.4 | 75.7 | 75.3 |
| Contact Angle (adv.) | 45 (6.6) | 58 (2.2) | 61 (4.3) | 62 (2.7) | 69 (2.6) | 65 (2.3) |
| Modulus (g/mm$^2$) | 90 (3) | 52 (1) | 53 (1) | 63 (3) | 66 (2) | 70 (3) |
| Tensile Strength (g/mm$^2$) | 134 (16) | 109 (18) | 100 (6) | 105 (11) | 87 (10) | 94 (18) |
| % Elongation (%) | 241 (30) | 197 (30) | 172 (7) | 151 (11) | 128 (11) | 128 (17) |
| Diameter | 13.803 | 14.203 | 14.162 | 13.850 | 13.794 | 13.706 |
| Sag | 3.972 | 4.090 | 3.892 | 3.804 | 3.684 | 3.698 |

The resultant monomeric mixture was cast into contact lenses by introducing the monomer mixture to a polypropylene mold assembly. Then, the mold assembly and monomer mixture were thermally cured for about 3 hours to form a contact lens. The resultant contact lenses were released from the mold assembly.

Examples 1-4

A monomer mix was made by mixing the following components, listed in Table 2 at amounts per weight.

TABLE 2

| Formulation | Ex. 1 | Ex. 2 | Ex.3 | Ex. 4 |
|---|---|---|---|---|
| NVP | 90 | 90 | 90 | 90 |
| TBE | 10 | 10 | 10 | 10 |
| HEMA | 0.5 | 0.5 | 0.5 | 0.5 |
| EGDMA | 0.13 | 0.13 | 0.13 | 0.13 |
| CIX-4 | 0.75 | 1 | 0.25 | 0 |
| Poloxamer 407 Dimethacrylate | 1 | 1 | 1 | 1 |
| SA Monomer | 3.16 | 3.16 | 3.16 | 3.16 |
| Propylene Glycol | 10 | 10 | 10 | 10 |
| Vazo 64 | 0.5 | 0.5 | 0.5 | 0.5 |
| TINT | 0.02 | 0.02 | 0.02 | 0.02 |

TABLE 2-continued

| Formulation | Ex. 1 | Ex. 2 | Ex.3 | Ex. 4 |
|---|---|---|---|---|
| Properties | | | | |
| Water Content (%) | 75.1 | 76.5 | 79 | 80.5 |
| Contact Angle (adv.) | 42 (1.4) | 38 (1.1) | 36 (0.1) | 35 (1.6) |
| Modulus (g/mm$^2$) | 73 (1) | 72 (3) | 89 (3) | 173 (15) |
| Tensile Strength (g/mm$^2$) | 155 (13) | 162 (16) | 147 (11) | 159 (9) |
| % Elongation (%) | 163 (14) | 177 (16) | 165 (17) | 158 (11) |
| Tear Strength (gf/mm) | 3.59 (0.23) | 4.53 (0.25) | 5.65 (0.27) | 8.46 (0.80) |
| Diameter | 13.881 | 13.963 | 14.186 | 13.815 |
| Sag | 3.813 | 3.889 | 3.758 | 3.685 |

The resultant monomeric mixture was cast into contact lenses by introducing the monomer mixture to a polypropylene mold assembly. Then, the mold assembly and monomer mixture were thermally cured for about 3 hours to form a contact lens. The resultant contact lenses were released from the mold assembly.

Examples 5-8

A monomer mix was made by mixing the following components, listed in Table 3 at amounts per weight.

TABLE 3

| Formulation | Ex. 5 | Ex. 6 | Ex. 7 | Ex. 8 |
|---|---|---|---|---|
| NVP | 90 | 90 | 90 | 90 |
| TBE | 10 | 10 | 10 | 10 |
| HEMA | 0.5 | 0.5 | 0.5 | 0.5 |
| EGDMA | 0.13 | 0.13 | 0.13 | 0.13 |
| CIX-4 | 0.75 | 0.5 | 0.25 | 0 |
| Poloxamer 407 Dimethacrylate | 1 | 1 | 1 | 1 |
| SA Monomer | 3.16 | 3.16 | 3.16 | 3.16 |
| Propylene Glycol | 10 | 10 | 10 | 10 |
| Vazo 64 | 0.50 | 0.50 | 0.50 | 0.50 |
| Reactive Blue Tint | 0.02 | 0.02 | 0.02 | 0.02 |
| Properties | | | | |
| Water Content (%) | 77.59 | 78.36 | 79.07 | 79.72 |
| Contact Angle Adv. | 48 (0.6) | 41 (3.0) | 37 (1.2) | 36 (1.8) |
| Modulus (g/mm$^2$) | 66 (2) | 71 (3) | 91 (5) | 203 (15) |

TABLE 3-continued

| Formulation | Ex. 5 | Ex. 6 | Ex. 7 | Ex. 8 |
|---|---|---|---|---|
| Tensile Strength (g/mm$^2$) | 150 (15) | 153 (17) | 172 (3) | 174 (13) |
| % Elongation (%) | 169 (18) | 172 (22) | 197 (6) | 173 (14) |
| Dimensions | 14.007 | 14.158 | 14.048 | 13.447 |
| Sag | 3.856 | 4.015 | 4.075 | 4.133 |

The resultant monomeric mixture was cast into contact lenses by introducing the monomer mixture to a polypropylene mold assembly. Then, the mold assembly and monomer mixture were thermally cured for about 3 hours to form a contact lens. The resultant contact lenses were released from the mold assembly.

Examples 9-13

A monomer mix was made by mixing the following components, listed in Table 4 at amounts per weight.

TABLE 4

| Formulation | Ex. 9 | Ex. 10 | Ex. 11 | Ex. 12 | Ex. 13 |
|---|---|---|---|---|---|
| NVP | 90 | 90 | 90 | 90 | 90 |
| TBE | 10 | 10 | 10 | 10 | 10 |
| HEMA | 0.5 | 0.5 | 0.5 | 0.5 | 0.5 |
| EGDMA | 0.13 | 0.13 | 0.13 | 0.13 | 0.13 |
| CIX-4 | 0.5 | 1 | 1.5 | 2 | 3 |
| Poloxamer 407 Dimethacrylate | 1 | 1 | 1 | 1 | 1 |
| SA Monomer | 2 | 2 | 2 | 2 | 3.16 |
| Propylene Glycol | 10 | 10 | 10 | 10 | 10 |
| Vazo 64 | 0.5 | 0.5 | 0.5 | 0.5 | 0.5 |
| TINT | 0.02 | 0.02 | 0.02 | 0.02 | 0.02 |
| Properties | | | | | |
| Water Content (%) | 79.62 | 77.24 | 75.67 | 74.62 | 70.68 |
| Contact Angle (adv.) | 39 (1.6) | 51 (1.0) | 56 (3.0) | 62 (1.9) | 62 (1.8) |
| Modulus (g/mm$^2$) | 58 (2) | 63 (1) | 75 (2) | 87 (2) | 137 (2) |
| Tensile Strength (g/mm$^2$) | 143 (12) | 121 (28) | 125 (8) | 100 (19) | 86 (20) |

TABLE 4-continued

| Formulation | Ex. 9 | Ex. 10 | Ex. 11 | Ex. 12 | Ex. 13 |
|---|---|---|---|---|---|
| % Elongation (%) | 193 (17) | 147 (32) | 131 (8) | 100 (15) | 61 (11) |
| Diameter | 14.439 | 14.115 | 13.636 | 13.443 | 12.900 |
| Sag | 3.827 | 3.914 | 3.784 | 3.669 | 3.493 |

The resultant monomeric mixture was cast into contact lenses by introducing the monomer mixture to a polypropylene mold assembly. Then, the mold assembly and monomer mixture were thermally cured for about 3 hours to form a contact lens. The resultant contact lenses were released from the mold assembly.

Examples 14-19

A monomer mix was made by mixing the following components, listed in Table 5 at amounts per weight.

TABLE 5

| Formulation | Ex. 14 | Ex. 15 | Ex. 16 | Ex. 17 | Ex. 18 | Ex. 19 |
|---|---|---|---|---|---|---|
| NVP | 90 | 90 | 90 | 90 | 90 | 90 |
| TBE | 10 | 10 | 10 | 10 | 10 | 10 |
| HEMA | 0.5 | 0.5 | 0.5 | 0.5 | 0.5 | 0.5 |
| EGDMA | 0.13 | 0.13 | 0.13 | 0.13 | 0.13 | 0.13 |
| CIX-4 | 1.25 | 1.5 | 1.75 | 2 | 3 | 1 |
| Poloxamer 407 Dimethacrylate | 1 | 1 | 1 | 1 | 1 | 1 |
| SA Monomer | 3.16 | 3.16 | 3.16 | 3.16 | 3.16 | 3.16 |
| Propylene Glycol | 10 | 10 | 10 | 10 | 10 | 10 |
| Vazo 64 | 0.50 | 0.50 | 0.50 | 0.50 | 0.50 | 0.50 |
| Reactive Blue Tint | 0.02 | 0.02 | 0.02 | 0.02 | 0.02 | 0.02 |
| Properties | | | | | | |
| Water Content (%) | 75.33 | 74.62 | 73.74 | 73.31 | 71.16 | 76.12 |
| Contact Angle Adv. | 56 (4.5) | 61 (4.4) | 64 (5.5) | 64 (2.7) | 63 (1.0) | 53 (1.0) |
| Modulus (g/mm$^2$) | 77 (0.4) | 84 (2) | 92 (2) | 97 (1) | 124 (3) | 83 (4) |
| Tensile Strength (g/mm$^2$) | 131 (10) | 124 (22) | 111 (19) | 105 (21) | 92 (17) | 141 (22) |
| % Elongation (%) | 134 (9) | 117 (17) | 103 (15) | 94 (16) | 71 (12) | 133 (15) |
| Dimensions | 13.661 | 13.556 | 13.422 | 13.160 | 12.991 | 13.447 |
| Sag | 3.755 | 3.709 | 3.703 | 3.675 | 3.480 | 3.818 |

The resultant monomeric mixture was cast into contact lenses by introducing the monomer mixture to a polypropylene mold assembly. Then, the mold assembly and monomer mixture were thermally cured for about 3 hours to form a contact lens. The resultant contact lenses were released from the mold assembly.

Examples 20-23

A monomer mix was made by mixing the following components, listed in Table 6 at amounts per weight.

TABLE 6

| Formulation | Ex. 20 | Ex. 21 | Ex. 22 | Ex. 23 |
|---|---|---|---|---|
| NVP | 90 | 80 | 70 | 60 |
| DMA | 0 | 10 | 20 | 30 |
| TBE | 10 | 10 | 10 | 10 |
| HEMA | 0.5 | 0.5 | 0.5 | 0.5 |
| EGDMA | 0.13 | 0.13 | 0.13 | 0.13 |
| CIX-4 | 1 | 1 | 1 | 1 |
| Poloxamer 407 Dimethacrylate | 1 | 1 | 1 | 1 |

TABLE 6-continued

| Formulation | Ex. 20 | Ex. 21 | Ex. 22 | Ex. 23 |
|---|---|---|---|---|
| SA Monomer | 3.16 | 3.16 | 3.16 | 3.16 |
| Propylene Glycol | 10 | 10 | 10 | 10 |
| Vazo 64 | 0.5 | 0.5 | 0.5 | 0.5 |
| TINT | 0.02 | 0.02 | 0.02 | 0.02 |
| Properties | | | | |
| Water Content (%) | 75.72 | 79.14 | 79.45 | 79.84 |
| Contact Angle (adv.) | 47 (1.7) | 70 (5.6) | 71 (4.4) | 73 (5.2) |
| Modulus (g/mm$^2$) | 79 (3) | 26 (1) | 21 (2) | 20 (1) |
| Tensile Strength (g/mm$^2$) | 155 (20) | 35 (10) | 32 (4) | 20 (11) |
| % Elongation (%) | 149 (20) | 167 (34) | 177 (17) | 121 (55) |
| Tear Strength (gf/mm) | 3.6 (0.2) | 2.1 (0.1) | 1.8 (0.2) | 1.5 (0.1) |
| Diameter | 13.654 | 14.260 | 14.324 | 14.387 |
| Sag | 3.856 | 3.900 | 3.959 | 3.972 |

The resultant monomeric mixture was cast into contact lenses by introducing the monomer mixture to a polypropylene mold assembly. Then, the mold assembly and monomer mixture were thermally cured for about 3 hours to form a contact lens. The resultant contact lenses were released from the mold assembly.

Examples 24-28

A monomer mix was made by mixing the following components, listed in Table 7 at amounts per weight.

TABLE 7

| Formulation | Ex. 24 | Ex. 25 | Ex. 26 | Ex. 27 | Ex. 28 |
|---|---|---|---|---|---|
| NVP | 90 | 87.5 | 85 | 82.5 | 80 |
| DMA | 0 | 2.5 | 5 | 7.5 | 10 |
| TBE | 10 | 10 | 10 | 10 | 10 |
| HEMA | 0.5 | 0.5 | 0.5 | 0.5 | 0.5 |
| EGDMA | 0.13 | 0.13 | 0.13 | 0.13 | 0.13 |
| CIX-4 | 1 | 1 | 1 | 1 | 1 |
| Poloxamer 407 Dimethacrylate | 1 | 1 | 1 | 1 | 1 |
| SA monomer | 3.16 | 3.16 | 3.16 | 3.16 | 3.16 |
| Propylene Glycol | 10 | 10 | 10 | 10 | 10 |
| Vazo 64 | 0.50 | 0.50 | 0.50 | 0.50 | 0.50 |
| Tint | 0.02 | 0.02 | 0.02 | 0.02 | 0.02 |
| Properties | | | | | |
| Modulus (g/mm$^2$) | 75 | 50 | 36 | 29 | 21 |
| Tensile Strength (g/mm$^2$) | 130 | 91 | 54 | 31 | 29 |
| % Elongation (%) | 136 | 166 | 166 | 129 | 166 |
| Water Content (%) | 75.98 | 77.49 | 78.43 | 78.8 | 80.11 |
| Contact Angle Adv. | 42 | 49 | 69 | 71 | 70 |

TABLE 7-continued

| Formulation | Ex. 24 | Ex. 25 | Ex. 26 | Ex. 27 | Ex. 28 |
|---|---|---|---|---|---|
| Diameter | 13.812 | 14.074 | 14.254 | 14.418 | 14.725 |
| Sag | 3.693 | 3.856 | 3.888 | 3.957 | 4.049 |

The resultant monomeric mixture was cast into contact lenses by introducing the monomer mixture to a polypropylene mold assembly. Then, the mold assembly and monomer mixture were thermally cured for about 3 hours to form a contact lens. The resultant contact lenses were released from the mold assembly.

Examples 29-31

A monomer mix was made by mixing the following components, listed in Table 8 at amounts per weight.

TABLE 8

| Formulation | Ex. 29 | Ex. 30 | Ex. 31 |
|---|---|---|---|
| NVP | 90 | 89 | 87.5 |
| DMA | 0 | 1 | 2.5 |
| TBE | 10 | 10 | 10 |
| HEMA | 0.5 | 0.5 | 0.5 |
| EGDMA | 0.13 | 0.13 | 0.13 |
| CIX-4 | 1 | 1 | 1 |
| Poloxamer 407 Dimethacrylate | 1 | 1 | 1 |
| SA monomer | 3.16 | 3.16 | 3.16 |
| Propylene Glycol | 10 | 10 | 10 |
| Vazo 64 | 0.50 | 0.50 | 0.50 |
| Tint | 0.02 | 0.02 | 0.02 |
| Properties | | | |
| Modulus (g/mm$^2$) | 77 | 68 | 50 |
| Tensile Strength (g/mm$^2$) | 154 | 135 | 90 |
| % Elongation (%) | 156 | 163 | 157 |
| Water Content (%) | 76.26 | 76.42 | 77.72 |
| Contact Angle Adv. | 40 | 47 | 49 |
| Diameter | 13.699 | 13.889 | 14.05 |
| Sag | 3.781 | 3.75 | 3.867 |

The resultant monomeric mixture was cast into contact lenses by introducing the monomer mixture to a polypropylene mold assembly. Then, the mold assembly and monomer mixture were thermally cured for about 3 hours to form a contact lens. The resultant contact lenses were released from the mold assembly.

Examples 32-37

A monomer mix was made by mixing the following components, listed in Table 9 at amounts per weight.

TABLE 9

| Formulation | Ex. 32 | Ex. 33 | Ex. 34 | Ex. 35 | Ex. 36 | Ex. 37 |
|---|---|---|---|---|---|---|
| NVP | 90 | 90 | 90 | 90 | 90 | 90 |
| DMA | 0 | 1 | 1.5 | 2 | 2.5 | 3 |
| TBE | 10 | 10 | 10 | 10 | 10 | 10 |
| HEMA | 0.5 | 0.5 | 0.5 | 0.5 | 0.5 | 0.5 |
| EGDMA | 0.13 | 0.13 | 0.13 | 0.13 | 0.13 | 0.13 |
| CIX-4 | 1 | 1 | 1 | 1 | 1 | 1 |
| Poloxamer 407 Dimethacrylate | 1 | 1 | 1 | 1 | 1 | 1 |
| SA monomer | 3.16 | 3.16 | 3.16 | 3.16 | 3.16 | 3.16 |
| Propylene Glycol | 10 | 10 | 10 | 10 | 10 | 10 |
| Vazo 64 | 0.50 | 0.50 | 0.50 | 0.50 | 0.50 | 0.50 |
| Tint | 0.02 | 0.02 | 0.02 | 0.02 | 0.02 | 0.02 |

TABLE 9-continued

| Formulation | Ex. 32 | Ex. 33 | Ex. 34 | Ex. 35 | Ex. 36 | Ex. 37 |
|---|---|---|---|---|---|---|
| Properties | | | | | | |
| Modulus (g/mm$^2$) | 75 | 63 | 59 | 49 | 49 | 45 |
| Tensile Strength (g/mm$^2$) | 144 | 129 | 121 | 112 | 88 | 80 |
| % Elongation (%) | 151 | 162 | 169 | 181 | 158 | 161 |
| Water Content (%) | 75.9 | 76.6 | 77.0 | 77.5 | 77.5 | 77.8 |
| Contact Angle (adv.) | 41 | 47 | 46 | 50 | 52 | 55 |
| Diameter | 13.798 | 13.842 | 13.836 | 14.055 | 14.008 | 14.06 |
| Sag | 3.56 | 3.634 | 3.67 | 3.704 | 3.699 | 3.739 |
| RI | 1.3774 | 1.3763 | 1.3752 | 1.3737 | 1.3741 | 1.3747 |

The resultant monomeric mixture was cast into contact lenses by introducing the monomer mixture to a polypropylene mold assembly. Then, the mold assembly and monomer mixture were thermally cured for about 3 hours to form a contact lens. The resultant contact lenses were released from the mold assembly.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. An ophthalmic device which is a polymerization product of a monomeric mixture comprising:
   (a) a major amount of cyclic lactam;
   (b) a minor amount of one or more second non-silicone-containing hydrophilic monomers, wherein at least one of the one or more second non-silicone-containing hydrophilic monomers is a non-silicone-containing amide hydrophilic monomer;
   (c) one or more hydrophobic monomers; and
   (d) a crosslinking agent mixture comprising (i) one or more di-, tri- or tetra(meth)acrylate-containing crosslinking agents and (ii) one or more di-, tri- or tetracarbamate-containing crosslinking agents;
   wherein the ophthalmic device has an equilibrium water content of at least about 65 weight percent.

2. The ophthalmic device of claim 1, wherein the major amount of the cyclic lactam present in the monomeric mixture is an amount greater than about 80 weight percent, based on the total weight of the monomeric mixture.

3. The ophthalmic device of claim 1, wherein the cyclic lactam is selected from the group consisting of N-vinyl-2-pyrrolidone, N-vinyl caprolactam, N-vinyl-2-piperidone and mixtures thereof.

4. The ophthalmic device of claim 1, wherein the non-silicone-containing amide hydrophilic monomer is selected from the group consisting of an N,N-dimethylacrylamide, N,N-dimethylmethacrylamide, N-(2-hydroxyethyl)methacrylamide and mixtures thereof.

5. The ophthalmic device of claim 1, wherein the minor amount of the one or more second non-silicone-containing hydrophilic monomers present in the monomeric mixture is an amount of about 0.25 to about 10 weight percent, based on the total weight of the monomeric mixture.

6. The ophthalmic device of claim 1, wherein the one or more second non-silicone-containing hydrophilic monomers further include 2-hydroxyethyl methacrylate, glyceryl methacrylate, N-methacryloyl glycine, (2-hydroxy-3-methacryloylpropyl)-4-methoxy phenylether or mixtures thereof.

7. The ophthalmic device of claim 1, wherein the one or more hydrophobic monomers are represented by the structure of Formula I:

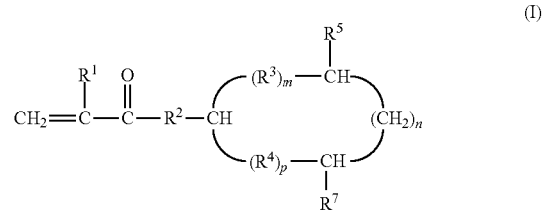

wherein R$^1$ is methyl or hydrogen; R$^2$ is —O— or —NH—; R$^3$ and R$^4$ are independently a divalent radical selected from the group consisting of —CH$_2$—, —CHOH— and —CHR$^6$—; R$^5$ and R$^6$ are independently a branched C$_3$-C$_8$ alkyl group; R$^7$ is hydrogen or —OH; n is an integer of at least 1, and m and p are independently 0 or an integer of at least 1, provided that the sum of m, p and n is 2, 3, 4 or 5.

8. The ophthalmic device of claim 1, wherein the one or more hydrophobic monomers are present in the monomeric mixture in an amount of about 0.5 to about 25 weight percent, based on the total weight of the monomeric mixture.

9. The ophthalmic device of claim 1, wherein the one or more di-, tri- or tetra(meth)acrylate-containing crosslinking agents are one or more alkanepolyol di-, tri- or tetra(meth)acrylate-containing crosslinking agents.

10. The ophthalmic device of claim 1, wherein the one or more di-, tri- or tetra(meth)acrylate-containing crosslinking agents are selected from the group consisting of an ethylene glycol di(meth)acrylate crosslinking agent having up to about 10 ethylene glycol repeating units, butanediol di(meth)acrylate crosslinking agent, trimethylol propane trimethacrylate crosslinking agent, pentaerythritol tetramethacrylate crosslinking agent and mixtures thereof.

11. The ophthalmic device of claim 1, wherein the one or more di-, tri- or tetracarbamate-containing crosslinking agents are selected from the group consisting of a di(N-vinylcarbamate)-containing crosslinking agent, a di(N-allylcarbamate)-containing crosslinking agent, a di(O-vinylcarbamate)-containing crosslinking agent, a di(O-allylcarbamate)-containing crosslinking agent, a tri(N-vinylcarbamate)-containing crosslinking agent, a tri(N-allylcarbamate)-containing crosslinking agent, a tri(O- vinylcarbamate)-containing crosslinking agent, a tri(O-allylcarbamate)-containing crosslinking agent, a tetra(N-vinylcarbamate)-containing crosslinking agent, a tetra (N-allylcarbamate)-containing crosslinking agent, a tetra(O-vinylcarbamate)-containing crosslinking agent, a tetra(O-allylcarbamate)-containing crosslinking agent, and mixtures thereof.

12. The ophthalmic device of claim 1, wherein the one or more di-carbamate-containing crosslinking agents are selected from the group consisting of diethylene glycol bis(N-vinylcarbamate), diethylene glycol bis(N-allylcarbamate), diethyl ene glycol bis(O-vinylcarbamate), diethylene glycol bis(O-allylcarbamate), and mixtures thereof.

13. The ophthalmic device of claim 1, wherein the one or more di-, tri- or tetra(meth)acrylate-containing crosslinking agents are present in the monomeric mixture in an amount of about 0.1 to about 10.0 weight percent, based on the total weight of the monomeric mixture, and the one or more di-, tri- or tetracarbamate-containing crosslinking agents are present in the monomeric mixture in an amount of about 0.1 to about 5.0 weight percent, based on the total weight of the monomeric mixture.

14. The ophthalmic device of claim 1, wherein the monomeric mixture further comprises one or more polymerizable surfactants selected from the group consisting of a poloxamer di(meth)acrylate, a reverse poloxamer di(meth)acrylate, a poloxamine di(meth)acrylate, a reverse poloxamine di(meth)acrylate and mixtures thereof.

15. The ophthalmic device of claim 1, wherein the monomeric mixture further comprises an ultraviolet (UV) blocker.

16. The ophthalmic device of claim 15, wherein the UV blocker is a compound of the formula

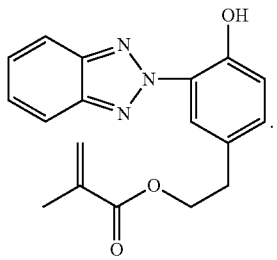 [SMILES: C=C(C)C(=O)OCCc1ccc(O)c(-n2nc3ccccc3n2)c1]

17. The ophthalmic device of claim 1, wherein the ophthalmic device is a contact lens.

18. The ophthalmic device of claim 1, wherein the ophthalmic device is a hydrogel.

19. The ophthalmic device of claim 1, wherein the monomeric mixture contains no silicone-containing monomer.

20. A method of making an ophthalmic device comprising
(a) providing a monomeric mixture comprising:
(i) a major amount of one or more first non silicone containing hydrophilic monomers a cyclic lactam;
(ii) a minor amount of one or more second non-silicone-containing hydrophilic monomers, wherein at least one of the one or more second non-silicone-containing hydrophilic monomers is a non-silicone-containing amide hydrophilic monomer;
(iii) one or more hydrophobic monomers; and
(iv) a crosslinking agent mixture comprising (1) one or more di-, tri- or tetra(meth)acrylate-containing crosslinking agents and (2) one or more di-, tri- or tetracarbamate-containing crosslinking agents;
(b) subjecting the monomeric mixture to polymerizing conditions to provide a polymerized device, and
(c) extracting the polymerized device;
wherein the ophthalmic device has an equilibrium water content of at least about 65 weight percent.

21. The method of claim 20, wherein the minor amount of the one or more second non-silicone-containing hydrophilic monomers present in the monomeric mixture is an amount of about 0.25 to about 10 weight percent, based on the total weight of the monomeric mixture.

22. The method of claim 20, wherein the cyclic lactam is selected from the group consisting of N-vinyl-2-pyrrolidone, N-vinyl caprolactam, N-vinyl-2-piperidone and mixtures thereof, and the non-silicone-containing amide hydrophilic monomer is selected from the group consisting of an N,N-dimethylacrylamide, N,N-dimethylmethacrylamide, N-(2-hydroxyethyl)methacrylamide and mixtures thereof.

23. The method of claim 20, wherein the one or more second non-silicone-containing hydrophilic monomers further include 2-hydroxyethyl methacrylate, glyceryl methacrylate, N-methacryloyl glycine, (2-hydroxy-3-methacryloylpropyl)-4-methoxy phenylether or mixtures thereof.

* * * * *

UNITED STATES PATENT AND TRADEMARK OFFICE
CERTIFICATE OF CORRECTION

PATENT NO. : 10,816,698 B2
APPLICATION NO. : 16/100693
DATED : October 27, 2020
INVENTOR(S) : Ivan M. Nuñez et al.

It is certified that error appears in the above-identified patent and that said Letters Patent is hereby corrected as shown below:

In the Claims

Claim 1, Column 21, Line 37, please insert --a-- before the word cyclic

Claim 1, Column 21, Line 38, please delete "second"

Claim 1, Column 21, Line 40, please delete "second"

Claim 5, Column 21, Line 64, please delete "second"

Claim 6, Column 22, Line 17, please delete "second"

Claim 20, Column 24, Lines 9-10, please delete "one or more first non silicone containing hydrophilic monomers"

Claim 20, Column 24, Line 11, please delete "second"

Claim 20, Column 24, Line 13, please delete "second"

Claim 21, Column 24, Line 27, please delete "second"

Claim 23, Column 24, Line 40, please delete "second"

Signed and Sealed this
Fifteenth Day of December, 2020

Andrei Iancu
*Director of the United States Patent and Trademark Office*